US006662942B1

United States Patent
Bonzagni

(10) Patent No.: US 6,662,942 B1
(45) Date of Patent: Dec. 16, 2003

(54) GLOVE PACKAGE

(75) Inventor: Maria A. Bonzagni, Marshfield, MA (US)

(73) Assignee: Acushnet Company, Fairhaven, MA (US)

( * ) Notice: Subject to any disclaimer, the term of this patent is extended or adjusted under 35 U.S.C. 154(b) by 0 days.

(21) Appl. No.: 10/160,613

(22) Filed: May 30, 2002

(51) Int. Cl.[7] .......................... B65D 85/00; B65D 85/18
(52) U.S. Cl. .................... 206/278; 206/459.5; 33/512; 33/2 R
(58) Field of Search .................... 33/511, 512, 2 R, 33/494, 514.2, 515, 549, 551, 17 R; 206/315.1, 278, 459.5

(56) References Cited

U.S. PATENT DOCUMENTS

| | | | | |
|---|---|---|---|---|
| 1,997,920 A | * | 4/1935 | Bliss | 33/2 R |
| 2,757,791 A | * | 8/1956 | Kendig | 206/292 |
| 2,776,772 A | * | 1/1957 | Itoda | 206/511 |
| 2,893,546 A | * | 7/1959 | Kendall et al. | 206/278 |
| 2,995,845 A | * | 8/1961 | Fraser | 206/278 |
| 3,347,411 A | * | 10/1967 | Kalata et al. | 206/519 |
| 3,442,420 A | * | 5/1969 | Edwards | 206/520 |
| 3,784,052 A | * | 1/1974 | Edwards | 206/520 |
| 3,837,476 A | * | 9/1974 | Schwartz | 206/278 |
| 4,173,074 A | | 11/1979 | Newman et al. | 33/2 R |
| 4,360,972 A | | 11/1982 | Montgomery | 33/17 R |
| 4,897,924 A | | 2/1990 | Tepley | 33/2 R |
| 5,522,499 A | * | 6/1996 | DeBiasio et al. | 206/278 |
| 6,050,420 A | | 4/2000 | Green | 206/764 |
| 6,327,787 B1 | | 12/2001 | Bonzagni et al. | 33/512 |
| 6,371,290 B1 | * | 4/2002 | Yearous et al. | 206/278 |

* cited by examiner

Primary Examiner—Diego Gutierrez
Assistant Examiner—Madeline Gonzalez
(74) Attorney, Agent, or Firm—D. Michael Burns

(57) ABSTRACT

A blister type packaging, housing at least one golf glove, has a device and indicia incorporated within the package whereby a user may estimate his/her glove size by merely placing his/her hand on a measuring station that will determine glove size by the length of the middle finger. The package will have incorporated a stop-tab, that the user will wedge between the web junction of his/her index and middle fingers, which will serve as a orientation or reference point for the correct positioning of the hand. The stop-tab is an integral part of the package, and helps to make the packages stackable with each other by nestling within the indentation of an adjoining package.

8 Claims, 4 Drawing Sheets

GLOVE PACKAGE

FIELD OF THE INVENTION

The present invention relates to a glove fitting device and method for measuring a user's hand and recommending an appropriate glove size based on the measurement. More specifically, the measuring device is part of the glove package.

BACKGROUND

In order to provide comfortable gloves for different users who have a variety of hand sizes, manufacturers generally provide consumers with a variety of different sized gloves. With respect to athletic gloves, such as those used in golf, proper glove fit is necessary for an additional reason. In such gloves, proper fit ensures that the glove does not interfere with the feel of a sports implement in the user's hands. Generally, gloves are produced in three size classifications, such as women's, men's, and cadet. Additionally, gloves within each size classification are usually produced in further size classifications, such as small, medium, large, extra-large, etc. Thus, retail locations often display a large number of different glove sizes and a customer often faces a time-consuming task of trying on multiple gloves in order to identify gloves with the best fit. Even so, this method is workable as long as the gloves are in a package that can be opened. Packaging such gloves is a blister type package has excellent marketing and retail sales benefits. The clear plastic blister allows the product to be seen without been handled or removed from the container. These type packages also reduce theft and are conducive to being displayed on racks and shelves.

A number of excellent instruments for measuring the hand size of people have been patented. Some drawbacks are that they may be too costly or else bulky thereby requiring space that may not be available. Others are extremely complicated and cannot be used by an inexperienced individual. Many people would prefer a more straightforward system that rapidly measures essential aspects of a customer's hand and accurately utilizes the measurements to suggest a glove size. For example, U.S. Pat. Nos. 1,997,920; 2,176,288; 2,605, 548; and 4,173,074 disclose devices that measure palm width and the length of only the longest finger.

Several references, such U.S. Pat. No. 4,897,924, teach of devices that measure the length of all of the fingers. Although these devices provide additional absolute information about the dimensions of a hand, such devices are generally too complicated and cumbersome to be used effectively in a retail setting.

Thus, a glove fitting device and method are needed that are easy for a customer to use in a retail setting, that do not require the package to be opened.

SUMMARY

The present invention includes a hand measuring device and method to aid a user in determining his/her glove size, especially as it relates to a golf glove. The device is integral within the packaging of the glove, and includes at least one measuring station on the back of the package. The package is of a standard blister type, with a see through plastic housing having at least one glove therein. The measuring station includes a hand outline with a reference point located at the web junction of the index and middle fingers and a scale of lines at the distal end of the fingers, each line indicating a different size glove. The user merely has to place his/her hand on the hand outline with the web junction of their hand pressed against the reference point. The length of the middle finger, by intersection with the lines of the scale, will indicate the glove size. The reference point comprises a stop tab that is an integral part of the blister mold. It comprises a plastic protrusion formed by the blister material.

Each individual package will contain either right or left handed men or ladies gloves and the back of the package will have a corresponding left or right hand measuring station.

Each blister package provides for a visual look of the glove without the need to open the package.

BRIEF DESCRIPTION OF THE FIGURES

Preferred features of the invention may be further understood by reviewing the following detailed description in conjunction with the appended drawing figures wherein.

DETAILED DESCRIPTION OF THE PREFERRED EMBODIMENT

Figures 1, 2:
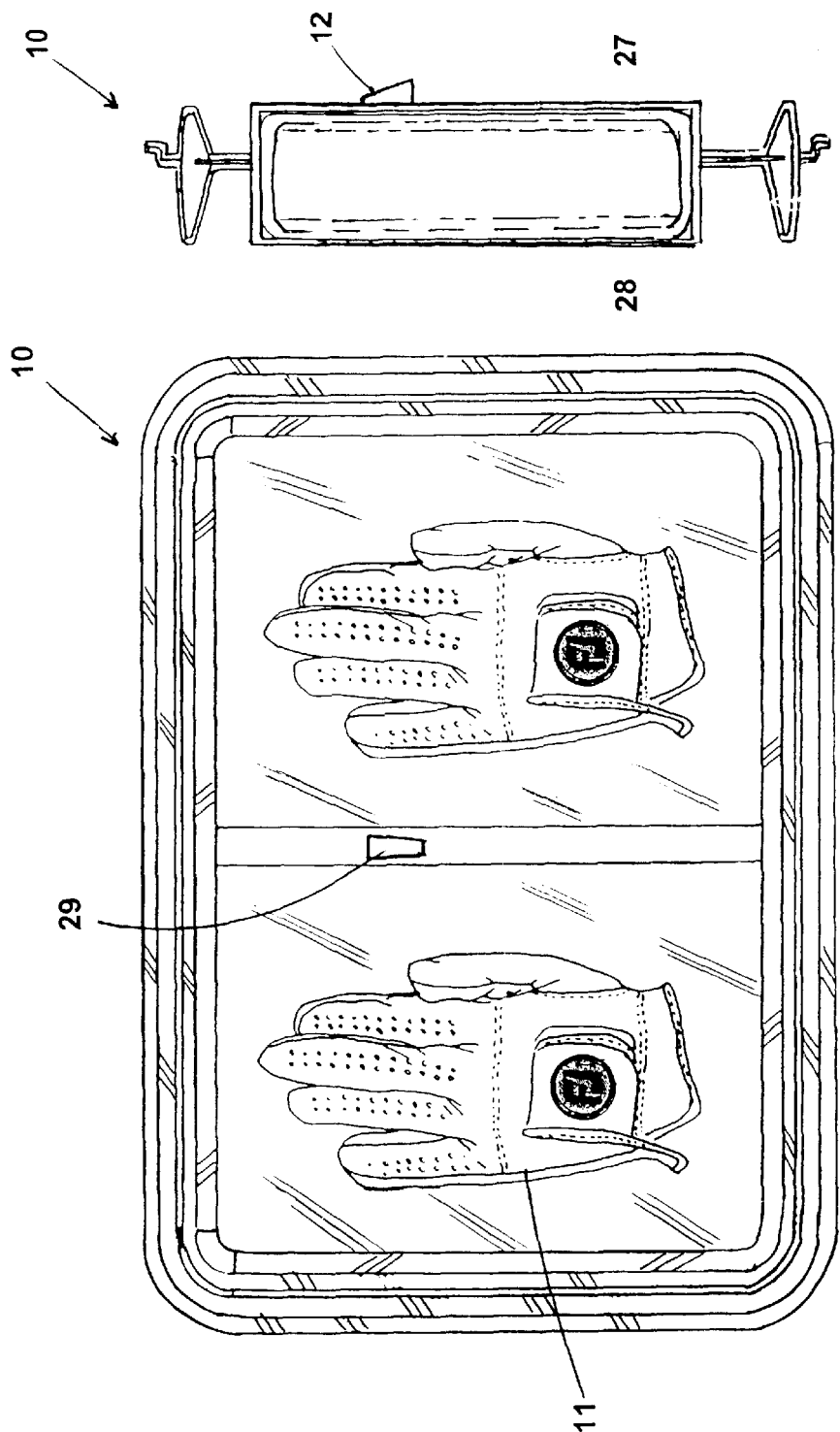
FIG. 1 is a front elevational view disclosing a blister package containing two golf gloves although one glove would suffice.
FIG. 2 is a side view of the package depicted in FIG. 1.
Figure 3:
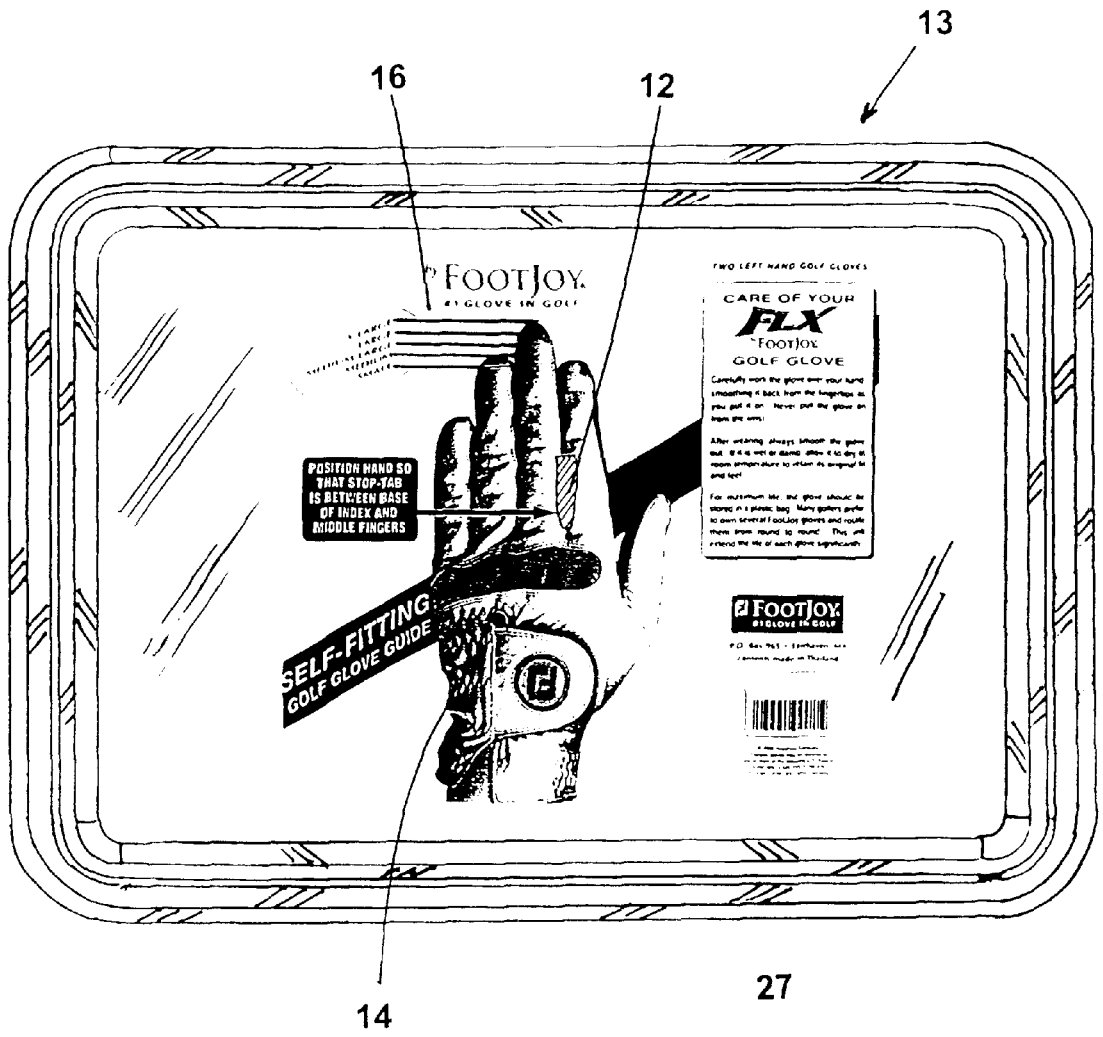
FIG. 3 is the rear elevation view of the package of FIG. 1 showing a left glove fitting measurement station.

In the FIGS. 1 and 2, there is shown the front surface 28 of a blister type package herein referred to as 10. Package 10 contains a pair of golf gloves 11 and a stop-tab 12 (to be discussed later). Referring to FIG. 3, the back surface 27 of package 10 depicts a measuring station 13 that is an integral part of package 10 and is included to aid an individual in correctly determining his/her proper glove size. The measuring station 13 shown in FIG. 3 happens to be for a left handed glove, however, it is to be appreciated that a right-handed measuring station would be but a mere image of it.

Figure 4:
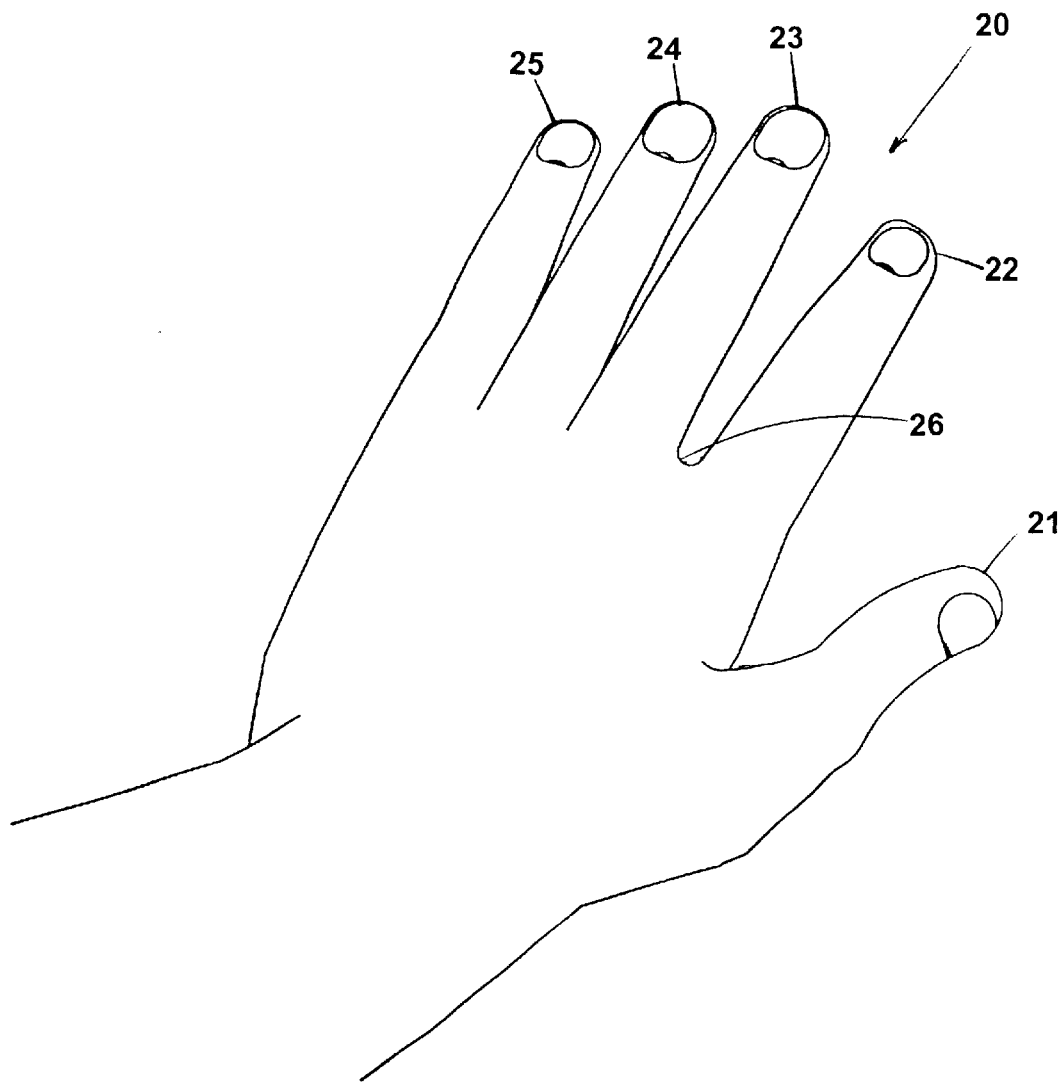
FIG. 4 is a perspective view of a typical hand.

Referring to FIG. 4, a typical human hand 20 comprises five digits including a thumb 21 and four fingers 22–25. Beginning with the thumb 21, and proceeding laterally across the hand, the five digits as used in the specification and claims are referred to as the thumb 21, index finger 22, middle finger 23, ring finger 24, and little finger 25. Finger web junction, such as 26, is located between the index and middle fingers 22 and 23. As described below, in FIG. 5, the measuring station 13, includes the glove outline 14, a middle finger 15, a reference point indicated by the stop tab 12 and a linear scale 16, wherein each line of the scale is correlated to a particular glove size.

Figure 5:
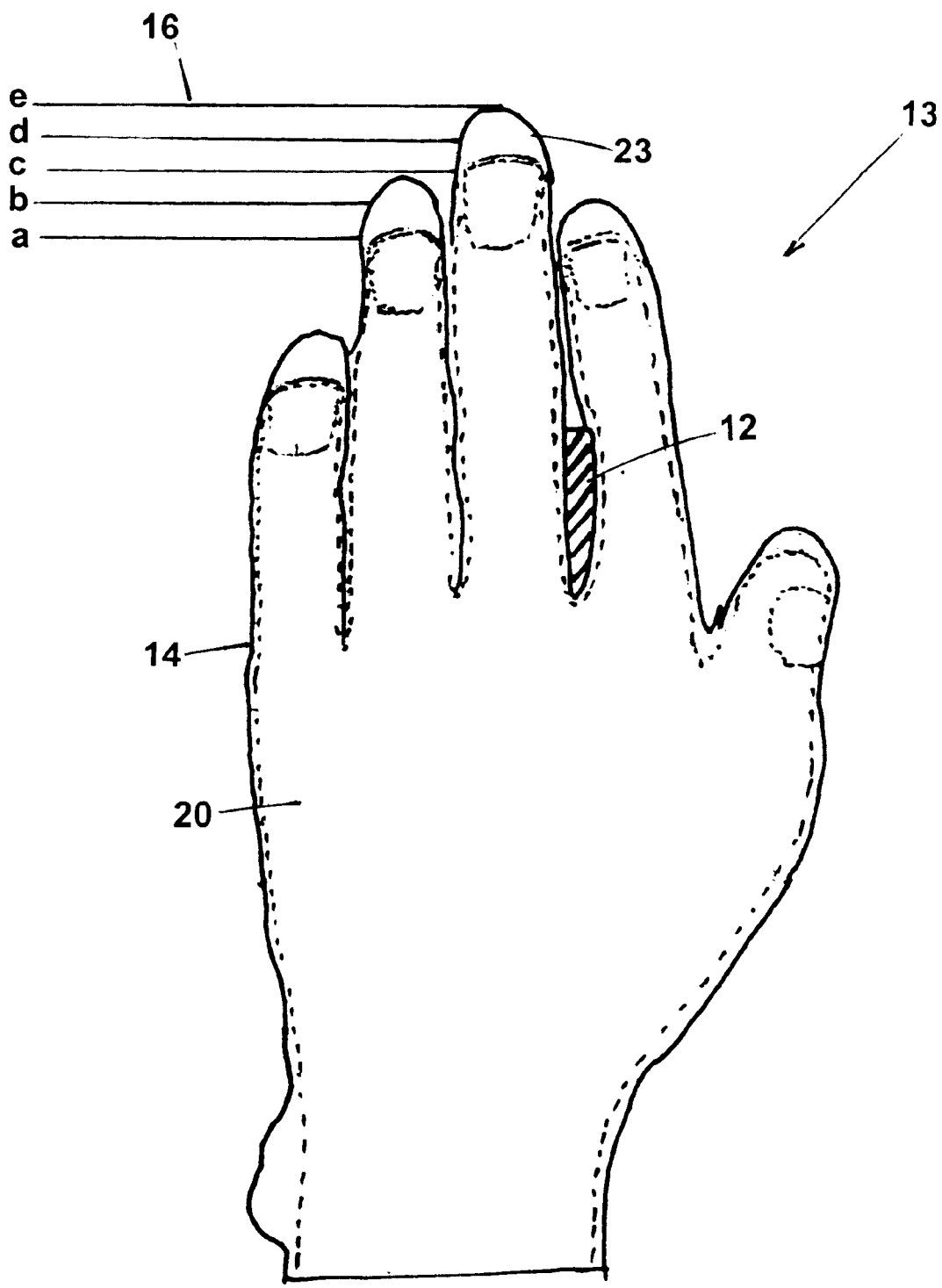
FIG. 5 is a front elevational view of the measurement station with a hand in phantom.

As illustrated on FIG. 5, the proper measurement position of the hand 20 (shown in phantom) placed on measurement station 13 occurs when the stop tab 12 contacts the web junction 26, and a longitudinal axis of the middle finger extends from the stop-tab 12. This position allows a finger tip length to determine a particular glove size. Stop-tab 12 is a protrusion that limits the forward movement of the hand 20, when hand 20 is placed on the measuring station 13. This allows for a glove size estimate. The stop-tab 12 is made by a punch through the plastic molding of the front surface 28 of the blister package 10 which therein extends through to protrude outwardly from the back surface 27 of package 10, leaving an indentation 29 in the front surface 28. In addition to the measurement function the stop-tab 12 serves as a stabilizer in the stacking of multiple packages. Each stop-tab 12 protrusion of the back surface 27 of a package nestling into the punch through indentation 29 on the front surface 28 of an adjoining package. Other methods of placing a stop-tab type device onto the measurement station 13 would be known to those skilled in the art.

In other embodiments, each hand measuring station may have additional stop-tabs configured to abut at least a portion of another or all of the web junctions between the other fingers, with multiple finger measurements taken to determine a glove size. Not shown, but of particular concern is a stop-tab between the index finger 22 and thumb 21.

As depicted in FIG. 5, measurement station 13 comprises linear scale 16 having a plurality of line measurements, a, b, c, d and e respectively. The lines a, b, c, d and e are substantially perpendicular to the longitudinal axis of the middle finger 23. Preferably, they are positioned so that middle finger 23 (shown in phantom on the glove outline 14), which when properly positioned against stop tab 12 is in alignment with one of corresponding lines a, b, c, d and e. Each line a–e corresponds to a glove size to which is indicated by the tip of middle finger 23. These glove sizes, can be small, medium, medium large, large, X-large, cadet, right or left handed, or some other type size description. Whether measurement station 13 is for women or for men depends on what gloves are packaged therein. If the package 10 contains women's gloves, then obviously the measurement station 13 would contain information as to women glove sizes.

Referring to FIG. 5, the method for determining a user's hand size is as follows: a user places her/his hand 20 (shown in phantom) on measurement station 13 so that web junction 26 abuts stop tab 14. The user determines his/her own glove size by seeing which corresponding line a–e the tip of their middle finger 23 most closely intersects. If the tip is located between two adjacent marks, the user should use the length value that is closest to the tip of the finger.

While it is apparent that the illustrative embodiments of the invention disclosed herein fulfill the objectives stated above, it is appreciated that numerous modifications and other embodiments may be devised by those skilled in the art. One such modification is that, although reference is made by the present invention towards measuring only the user's middle finger, it is to be appreciated that one of ordinary skill in the art will understand that the invention herein is not limited to measuring only the length of this one finger, but could readily be adapted to measuring the lengths or relative lengths of any combination of fingers and thumb. Therefore, it will be understood that the appended claims are intended to cover all such modifications and embodiments which would come within the true spirit and scope of the present invention.

I claim:

1. A package for a golf glove comprising:
   an opaque blister package containing at least one golf glove;
   the blister package having generally planar front and back surfaces;
   a reference point on stop-tab protruding from the back surface for orienting an individual's hand on a measuring station on the back surface; and
   a corresponding indentation on the front surface of the package;
   the indentation of a configuration for nesting together a stop-tab of an adjoining package to create stackable packages; and
   sizing indicia on the measuring station being visible from the back surface as an aid in selecting a proper sized glove.

2. The package of claim 1, wherein the protruding stop-tab is for positioning between webbing of an individual's adjacent fingers.

3. The package of claim 2, wherein the stop-tab is an integral part of the blister package.

4. The package of claim 2, wherein the adjacent fingers are the index finger and middle finger.

5. The package of claim 1, wherein the sizing indicia is for a left hand.

6. The package of claim 1, wherein the sizing indicia is for a right hand.

7. The hand measuring device of claim 1, the indicia comprising a linear scale for correlating a plurality of finger length values with a plurality of predetermined glove sizes.

8. The hand measuring device of claim 7, wherein the predetermined glove sizes comprise women's small, women's medium, women's medium-large, women's large, cadet small, cadet medium, cadet medium-large, cadet large, cadet extra-large, men's small, men's medium, men's medium-large, men's large, men's extra-large, men's extra-extra-large.

* * * * *